Dec. 7, 1948. L. SATTERFIELD Plant Pat. 813

PEACH TREE

Original Filed Sept. 26, 1945

INVENTOR

LAWRENCE SATTERFIELD, DECEASED

BY LUELLA SATTERFIELD, ADMINISTRATRIX

By Owen + Owen

Attorneys

Patented Dec. 7, 1948

Plant Pat. 813

UNITED STATES PATENT OFFICE

813

PEACH TREE

Lawrence Satterfield, deceased, late of Port Clinton, Ohio, by Luella Satterfield, administratrix, Port Clinton, Ohio Continuation of application Serial No. 618,612, September 26, 1945. This application May 16, 1946, Serial No. 670,060

1 Claim. (Cl. 47—62)

This relates to a variety of peach tree which is a sport of the J. H. Hale variety of peaches and most closely resembles that variety but differs therefrom in particulars which will be noted hereafter. The sport appeared in two branches of a J. H. Hale peach tree in an orchard at Port Clinton, Ohio, and the different character of these two branches became apparent in the fruiting season of 1930. The branches were reproduced by budding in 1932, and were planted in an orchard near Clyde, Ohio, beside trees of the old J. H. Hale variety. When the trees thus produced matured, they were found to reproduce the characteristics of the branches and produce trees such as will be described below. No permission was granted for reproduction for unrestricted sale to the public, but the trees were kept under observation and their characteristics noted. An especial characteristics of the peaches, relating to canning, became apparent in the last canning season and it was thereupon determined to reproduce the peach tree in question and place it upon the market.

Figure 1:
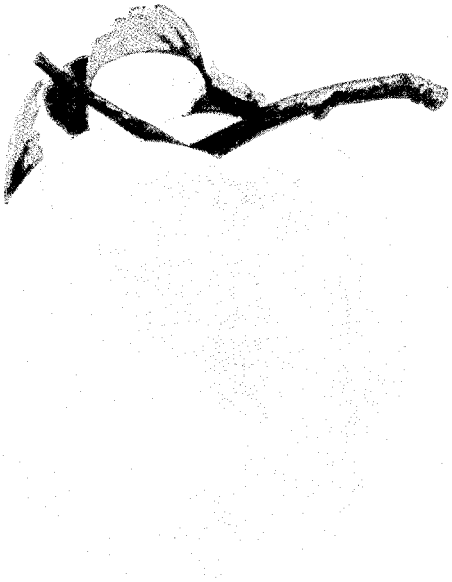
Figure 2:
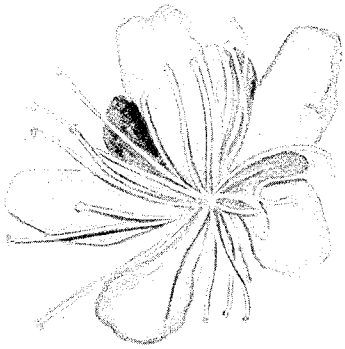
Figure 3:
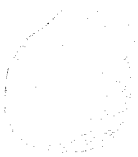

In the accompanying drawings constituting a part of this specification, Fig. 1 is a view of the fruit of the new peach tree, Fig. 2 is a view of the flower, and Fig. 3 is a view of a detached petal.

Trees of the new variety have been grown side by side with trees of the J. H. Hale variety. The new variety of peach tree is of medium size but larger than the J. H. Hale, being about the same size as the Elberta peach. It is a more vigorous and stronger grower than the J. H. Hale and is somewhat more upright than the J. H. Hale. It has proved hardier than the J. H. Hale and more productive, being about as productive as the Elberta. The trunk is smooth and stocky. The twigs have an average of 1.9 nodes, per inch, whereas J. H. Hale twigs grown under the same conditions have 1.5 nodes per inch.

The leaves averaged approximately six and one-fourth inches long and one and five-eighths inches wide, being a little wider than those of the J. H. Hale varety and not quite so long. They are obovate, lanceolate in shape and are thin and leathery. The upper surface is medium dark green and smooth. The lower surface is a grayish olive green, with a prominent midrib. The serrations on the margin of the leaf are medium in sharpness and often double-tipped with reddish brown glands. The petiole averages three-eighths of an inch long, thick and with uniform dark brown glands, varying in number from one to four, with occasionally five. The neighboring J. H. Hale leaves had petiole five-sixteenths of an inch long and glands varying in number from one to five.

The blooming period is about two days later than that of the J. H. Hale. The flowers average about three-quarters as large as those of the J. H. Hale in all gross morphological parts. The petals average approximately three-eighths of an inch long and are nearly round in shape, whereas J. H. Hale petals are distinctively oval in shape. The coloring is a darker pink at the margin of the petal than the J. H. Hale, and the stigma extends about one-sixteenth of an inch further beyond the anthers than does the stigma of the J. H. Hale.

The fruit ripens two or three days after the Elberta and the J. H. Hale. The fruit most nearly resembles that of the J. H. Hale variety, being similar in thickness of skin, but it has a finer texture and better flavor than the J. H. Hale. An especially notable characteristic is that, where the J. H. Hale has numerous undeveloped fruits or so-called "buttons," the new variety is substantially free from "buttons." The fruit is freestone, the flesh of the fruit is yellow, juicy, fine-grained, fine quality, with red about the pit. The color is lemon yellow overspread with dark red. The halves of the peach are equal, the cavity is deep, wide, and regular. The suture is shallow, with little depression. The apex is roundish.

The stone is one and five-eighths inches long and one and three-eighths inches wide, oval flattened at the base and pointed at the apex. Ventral suture is furrowed, deeply grooved along the sides; dorsal suture is winged, deeply grooved also.

An especial characteristic of the fruit is that the flesh retains its shape and is easy to handle in canning without damage to the evenly divided halves of the fruit, thus being easy to can in the desirable attractive halves. While the fruit has this firm characteristic, it is at the same time of very fine flavor, making a very good fresh fruit peach, and an especially good cannng fruit.

This application is a continuation of application 618,612, filed September 26, 1945, now abandoned.

It is claimed:

The variety of peach tree herein described and shown, having a tree that resembles the J. H. Hale more nearly than it resembles any other hitherto known variety, but which differs from said J. H. Hale by being larger in size, more vigorous and upright in growth and hardier, having leaves somewhat shorter and broader, blooming about two days later with blossoms about three-fourths the size of those of the J. H. Hale, with petals shaped and colored substantially as shown; having substantially no "buttons," with fruit ripening two or three days later than the J. H. Hale with similar fruit but finer in texture, better flavored, and with equal halves that hold their shape firmly.

LUELLA SATTERFIELD,

*Administratrix of the Estate of Lawrence Satterfield, Deceased.*

No references cited.